(12) United States Patent
Telang et al.

(10) Patent No.: US 8,283,332 B2
(45) Date of Patent: Oct. 9, 2012

(54) PFKFB4 INHIBITORS AND METHODS OF USING THE SAME

(75) Inventors: Sucheta Telang, Louisville, KY (US); Jason Chesney, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 12/761,773

(22) Filed: Apr. 16, 2010

(65) Prior Publication Data

US 2010/0267815 A1 Oct. 21, 2010

Related U.S. Application Data

(60) Provisional application No. 61/170,439, filed on Apr. 17, 2009.

(51) Int. Cl.
*A61K 48/00* (2006.01)
(52) U.S. Cl. .................................................. 514/44 R
(58) Field of Classification Search .................. 514/44 R
See application file for complete search history.

(56) References Cited

U.S. PATENT DOCUMENTS

| 7,709,616 B2 * | 5/2010 | Bentwich et al. ............ 536/23.1 |
| 2004/0180357 A1 * | 9/2004 | Reich et al. ........................ 435/6 |

FOREIGN PATENT DOCUMENTS

| WO | 99/07409 A1 | 2/1999 |
| WO | 99/32619 A1 | 7/1999 |
| WO | 00/01846 A1 | 1/2000 |
| WO | 00/44895 A1 | 8/2000 |
| WO | 00/44914 A1 | 8/2000 |
| WO | 01/29058 A1 | 4/2001 |
| WO | 01/36646 A1 | 5/2001 |

OTHER PUBLICATIONS

Bartrons et al. (J. Bioenerg. Biomembr. 2007, 39(3):223-229).*
Brenda Bass, "RNA Interference: The Short Answer," Nature, 411:428-429, May 24, 2001.
B. Clem et al., "Small-molecule inhibition of 6-phosphofructo-2-kinase activity suppresses glycolytic flux and tumor growth," Mol. Cancer Ther. 7:110-20 Jan. 2008.
Elbashir et al, "Duplexes of 21-nucleotide RNAs mediate RNA interference in cultured mammalian cells," Nature 411: 494-498, May 24, 2001.
O. Mischenko et al.,"Hypoxia induces transcription of 6-phosphofructo-2-kinase/fructose-2,6-biphosphatase-4 gene via hypoxia-inducible factor-1α activation," FEBS Lett., Aug. 30, 2004.
S. Telang et al., "Ras Transformation requires metabolic control by 6-phosphofructo-2-kinase," Oncogene, May 2006; 25:7225-7234.
Von Schaftingen et al., "A Kinetic Study of Pyrophosphate: Fructose-6-Phosphate Phosphotransferase from Potato Tubers: Application to a Microassay of Fructose 2,6-Bisphsophate," Eur J. Biochem 129: 191-195, 1982.

* cited by examiner

*Primary Examiner* — J. E. Angell
(74) *Attorney, Agent, or Firm* — Dinsmore & Shohl LLP

(57) ABSTRACT

Methods of reducing expression of 6-phosphofructo-2-kinase/fructose-2,6-bisphosphatase 4 (PFKFB4) and methods of treating a cancer in a cell are provided, the methods including contacting a cell with an effective amount of a PFKFB4 inhibitor. Short hairpin RNA (shRNA) and small interfering RNA (siRNA) inhibitors of PFKFB4 and their methods of use are also provided.

13 Claims, 5 Drawing Sheets

A.

B.

C.

D.

SEQUENCE LISTING

```
<160> NUMBER OF SEQ ID NOS: 15

<210> SEQ ID NO 1
<211> LENGTH: 17
<212> TYPE: DNA
<213> ORGANISM: Homo sapiens
```

```
<220> FEATURE:
<221> NAME/KEY: misc_feature
<222> LOCATION: (1)..(17)
<223> OTHER INFORMATION: PFKFB4 gene fragment

<400> SEQUENCE: 1
cacttgtatg gtcctgt                                                        17

<210> SEQ ID NO 2
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: PFKFB4 gene fragment

<400> SEQUENCE: 2
gagtcgctag atgaggacct ggata                                               25

<210> SEQ ID NO 3
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: PFKFB4 gene fragment

<400> SEQUENCE: 3
cacttgtatg gtcctgt                                                        17

<210> SEQ ID NO 4
<211> LENGTH: 64
<212> TYPE: DNA
<213> ORGANISM: Homo sapiens
<220> FEATURE:
<221> NAME/KEY: misc_feature
<222> LOCATION: (1)..(64)
<223> OTHER INFORMATION: shRNA inhibitor of PFKFB4

<400> SEQUENCE: 4
gatccgcact tgtatggtcc tgtaattcaa gagattacag gaccatacaa gtgttttttg         60
gaaa                                                                      64

<210> SEQ ID NO 5
<211> LENGTH: 64
<212> TYPE: DNA
<213> ORGANISM: Homo sapiens
<220> FEATURE:
<221> NAME/KEY: misc_feature
<222> LOCATION: (1)..(64)
<223> OTHER INFORMATION: shRNA inhibitor of PFKFB4

<400> SEQUENCE: 5
agcttttcca aaaacacttg gtatggtcct gtaatctctt gaattacagg accatacaag         60
tgcg                                                                      64

<210> SEQ ID NO 6
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: siRNA inhibitor of PFKFB4

<400> SEQUENCE: 6
```
ggagagcgac caucuuuaa                                              19

<210> SEQ ID NO 7
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: siRNA inhibitor of PFKFB4

<400> SEQUENCE: 7
uuaaagaugg ucgcucucc                                              19

<210> SEQ ID NO 8
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: siRNA inhibitor of PFKFB4

<400> SEQUENCE: 8
cacuuguaug guccuguaa                                              19

<210> SEQ ID NO 9
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: siRNA inhibitor of PFKFB4

<400> SEQUENCE: 9
uuacaggacc auacaagug                                              19

<210> SEQ ID NO 10
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: siRNA inhibitor of PFKFB4

<400> SEQUENCE: 10
auuauccuga auuccucgu agguc                                        25

<210> SEQ ID NO 11
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: siRNA inhibitor of PFKFB4

<400> SEQUENCE: 11
gaccuacgag gaaauucagg auaau                                       25

<210> SEQ ID NO 12
<211> LENGTH: 25
<212> TYPE: RNA
<213> ORGANISM: Homo sapiens
<220> FEATURE:
<221> NAME/KEY: misc_feature

```
<222> LOCATION: (1)..(25)
<223> OTHER INFORMATION: siRNA inhibitor of PFKFB4

<400> SEQUENCE: 12
uauccagguc cucaucuagc gacuc                                              25

<210> SEQ ID NO 13
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: siRNA inhibitor of PFKFB4

<400> SEQUENCE: 13
gagucgcuag augaggaccu ggaua                                              25

<210> SEQ ID NO 14
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: siRNA inhibitor of PFKFB4

<400> SEQUENCE: 14
ucucguugag gaccuuccac uguuc                                              25

<210> SEQ ID NO 15
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: siRNA inhibitor of PFKFB4

<400> SEQUENCE: 15
gaacagugga agguccucaa cgaga                                              25
```

US 8,283,332 B2

PFKFB4 INHIBITORS AND METHODS OF USING THE SAME

RELATED APPLICATION

This application claims the benefit of U.S. Provisional Application No. 61/170,439, filed Apr. 17, 2009, which application is hereby incorporated by reference in its entirety.

FIELD OF THE INVENTION

The presently-disclosed subject matter relates to 6-phosphofructo-2-kinase/fructose-2,6-bisphophatase 4 (PFKFB4) inhibitors and methods of using the same. In particular, the presently-disclosed subject matter relates to PFKFB4 inhibitors, including small interfering RNA (siRNA) and short hairpin RNA (5hRNA), and methods of using these inhibitors to reduce the expression of PFKFB4 and/or treat a cancer in a cell.

BACKGROUND OF THE INVENTION

Neoplastic cells preferentially utilize glycolysis to satisfy their increased needs for energy and biosynthetic precursors. The PFKFB enzymes (PFKFB 1-4) synthesize fructose-2,6-bisphosphate (F2,6BP) which activates 6-phosphofructo-1-kinase (PFK-1), an essential control point in the glycolytic pathway. Until recently, the PFKFB3 isozyme has been considered the principal source of the increased F2,6BP observed in cancer cells. However, new evidence indicates the co-expression of several PFKFB isozymes in transformed and untransformed tissues as well as increased expression of the PFKFB4 isoform in several neoplastic cell lines and in tumors.

Accordingly, there remains a need in the art for PFKFB4 inhibitors and methods of using the same that can effectively be used to target neoplastic cells, including the mechanisms within those cells that relate to the preferential use of the glycolytic pathway.

SUMMARY OF THE INVENTION

PFKFB4 inhibitors, including siRNA and shRNA inhibitors, and their methods of use in reducing expression of PFKFB4 and treating cancer are disclosed herein.

In one embodiment, a method of reducing expression of 6-phosphofructo-2-kinase/fructose-2,6-bisphosphatase 4 (PFKFB4) is provided, comprising contacting a cell with an effective amount of a PFKFB4 inhibitor.

In another embodiment, a method of treating a cancer in a cell is provided, comprising contacting a cell with an effective amount of a PFKFB4 inhibitor.

In another embodiment, an isolated nucleic acid comprising a sequence selected from the group consisting of SEQ ID NO: 4 and SEQ ID NO: 5 is provided.

In still another embodiment, an isolated nucleic acid comprising a sequence selected from the group consisting of SEQ ID NO: 6 and SEQ ID NO: 8 is provided.

In another embodiment, an isolated nucleic acid comprising a sequence selected from the group consisting of SEQ ID NO: 7 and SEQ ID NO: 9 is provided.

These and other objects, features, embodiments, and advantages will become apparent to those of ordinary skill in the art from a reading of the following detailed description and the appended claims.

DETAILED DESCRIPTION OF THE INVENTION

Figure 1:
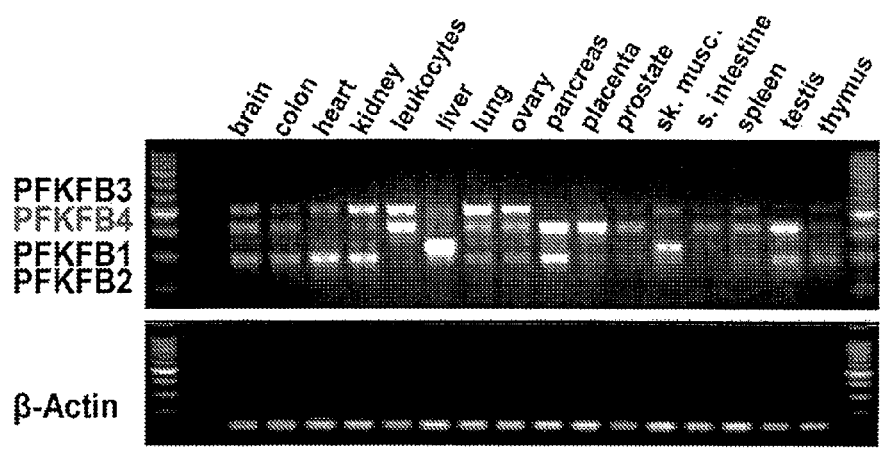
FIG. 1. PFKFB4 mRNA levels are increased in 17 of 20 analyzed human tumor tissues relative to adjacent normal tissues. (a) Sixteen human normal untransformed tissues were analyzed by multiplex RT-PCR for the simultaneous expression of all four PFKFB isozymes. PCR products were normalized to β-actin. (b) Matched tumor and adjacent normal tissues cDNA specimens from the lung (1), colon (2), breast (3) and ovary (4) were analyzed by multiplex RT-PCR for simultaneous expression of all four PFKFB isozymes by multiplex RT-PCR. PCR products were normalized to β-actin.
Figure 1:
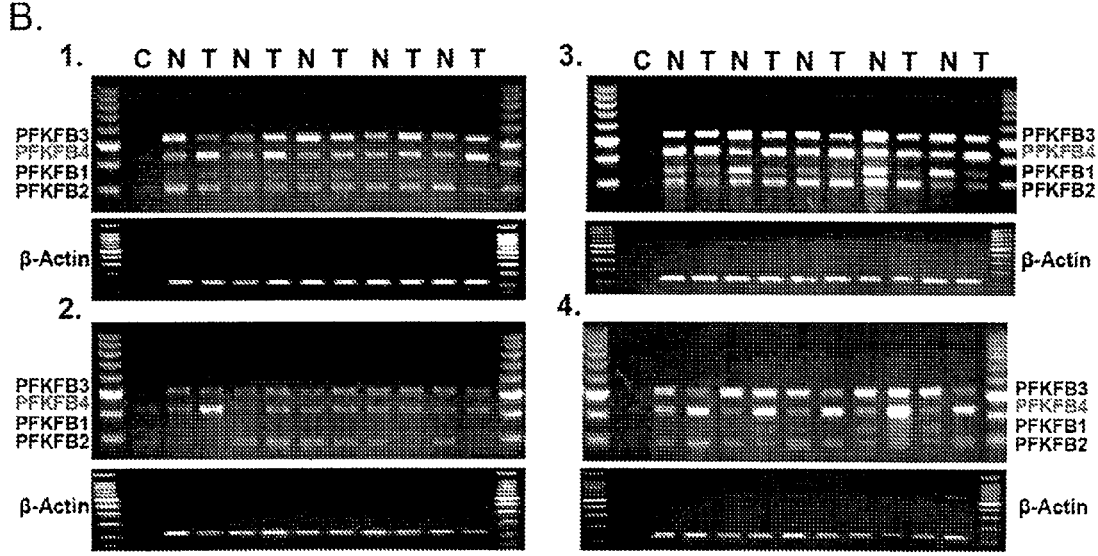

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The phenomenon of co-expression of the PFKFB enzymes in human neoplastic tissues indicates a relationship between the PFKFB isoforms the production of F2,6BP found in the cancer cell. The presently disclosed data indicate that the PFKFB4, or testis, isoform is upregulated in the majority of tumors examined relative to the other PFKFB enzymes. Silencing the PFKFB4 protein leads to a reduction in F2,6BP production, a decrease in glycolytic flux to lactate, and a significant inhibition of anchorage independent growth both in soft agar and in vivo. Thus, the data indicate a previously undemonstrated role for PFKFB4 in neoplastic transformation and tumorigenesis.

Previous studies have implicated PFKFB3 as the dominant source of F2,6BP and, thus, the principal PFKFB isoform responsible for regulation of glycolytic flux in neoplastic cells. Evidence however indicates a possible role for the PFKFB3 isoform in cell proliferation that is distinct from glycolysis. PFKFB3 is highly expressed in proliferating tissues in comparison with non-proliferating tissues and its expression is upregulated in response to including serum, insulin and progesterone. Additionally, recent data from Clem et al examining the effect of a small molecular inhibitor of PFKFB3 (3PO) have found that exposure of Jurkat T cell leukemia cells to the compound causes growth inhibition by cell cycle arrest at the G2/M phase (Clem, B. et al., Small-molecule inhibition of 6-phosphodructo-2-kinase activity suppresses glycolytic flux and tumor growth, *Mol. Cancer. Ther.* 7: 110-20 (2008)). These data suggest that another of the PFKFB isoforms may play a more important role in the control of glycolysis in a tumor.

The growth of neoplastic cells as a tumor requires the ability to thrive in a hypoxic environment. The metabolic adaptation of solid tumors is mediated in part by the transcription factor HIF-1 which promotes the transcription of genes encoding several glucose transporters and the majority of glycolytic enzymes. Minchenko et al recently found that exposure of several human transformed cell lines (PC-3, HeLa and Hep-3B) to hypoxia (1% oxygen) or the hypoxia mimic, dimethyloxalylglycine, caused the rapid induction of PFKFB4 mRNA species and that this induction was completely abrogated by deletion of the hypoxia-responsive element in the 5'-flanking sequence of PFKFB4 (Minchenko, O. et al., Hypoxia induces transcription of 6-phosphofructo-2-kinase/-2,6-bisphosphatase-4 gene via hypoxia-inducible factor-1alpha activation, *FEBS Lett.* 576:14-20 (2004)). These findings indicate that the induction of PFKFB4 mRNA may be an essential component of the HIF-1α mediated glycolytic adaptation to hypoxia. The presently disclosed data demonstrate that the reduction in F2,6BP caused by the knockdown of PFKFB4 protein in A549 cells causes an almost complete abrogation of anchorage independent growth in soft agar. A significant inhibition of the growth of the treated cells as tumors in vivo indicates that this isoform is important in the growth of cells as a three-dimensional structure similar to a tumor where proximity to oxygen and nutrients may be limited.

Further, the presently disclosed data demonstrate that the decrease in intracellular F2,6BP levels caused by silencing PFKFB4 led to a ~30% decrease in lactate secretion into the media. The A549 lung adenocarcinoma cells express three PFKFB isoforms (PFKFB2-4) and this relatively modest decrease in lactic acid secretion may be explained by compensation by the other isoforms. Interestingly, a dramatic inhibition of both anchorage independent growth in soft agar and as xenograft tumors in vivo was observed, indicating that although these transformed cells express two other PFKFB isoforms, the F2,6BP produced by the PFKFB4 isoform performs an important function in glycolytic flux.

Thus, the increased expression of the PFKFB4 isoform in multiple tumors is shown herein and further experiments demonstrate that silencing of the PFKFB4 protein results in a decrease in F2,6BP production, glycolytic flux to lactate and a decrease in anchorage independent growth both in vitro and in vivo.

Accordingly, the presently-disclosed subject matter includes PFKFB4 inhibitors and methods of using the same.

In one embodiment, a method of reducing expression of PFKFB4 is provided that comprises contacting a cell with an effective amount of a PFKFB4 inhibitor. As used herein, the term "PFKFB4 inhibitor" refers to a molecule that inhibits or otherwise decreases the expression of a PFKFB4 protein. As such, the term PFKFB4 inhibitor can refer to a molecule that decreases the expression level of a PFKFB4 gene, decreases a level of a PFKFB4 RNA molecule (e.g., mRNA), or decreases the activity of one or more PFKFB4 proteins or proteins subunits due to a down-regulation of the one or more PFKFB4 proteins or protein subunits, such that expression, level, or activity of a PFKFB4 protein is less than that observed in the absence of the PFKFB4 inhibitor.

The term "RNA" refers to a molecule comprising at least one ribonucleotide residue. By "ribonucleotide" is meant a nucleotide with a hydroxyl group at the 2' position of a ribofuranose moiety. The term encompasses double-stranded RNA, single-stranded RNA, RNAs with both double-stranded and single-stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently-disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The terms "small interfering RNA" or "siRNA" and "short hairpin RNA" or "shRNA" are used herein to refer to any nucleic acid molecule capable of mediating RNA interference (RNAi) or gene silencing. See e.g., Bass, Nature 411:428-429, 2001; Elbashir et al., Nature 4 11:494-498, 2001a; and PCT International Publication Nos. WO 00/44895, WO 01/36646, WO 99/32619, WO 00/01846, WO 01/29058, WO 99/07409, and WO 00/44914. In some embodiments, an siRNA or shRNA is provided that comprises a double-stranded polynucleotide molecule comprising complementary sense and antisense regions, wherein the antisense region comprises a sequence complementary to a region of a target nucleic acid molecule (for example, a nucleic acid molecule encoding PFKFB4). In another embodiment, an siRNA or shRNA is provided that comprises a single stranded polynucleotide having self-complementary sense and antisense regions, wherein the antisense region comprises a sequence complementary to a region of a target nucleic acid molecule. In another embodiment, an siRNA or shRNA molecule can be provided that comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA or shRNA capable of mediating RNAi. As used herein, siRNA or shRNA molecules need not be limited to those molecules containing only RNA, but further encompass chemically modified nucleotides and non-nucleotides.

In some embodiments of the presently-disclosed subject matter, a method of reducing expression of PFKFB4 is provided, wherein the PFKFB4 inhibitor is an siRNA. In some embodiments, the siRNA is double-stranded. In some embodiments, the siRNA is designed against a PFKFB4 gene or fragments thereof. For example, in some embodiment, the siRNA is designed against a nucleic acid sequence comprising SEQ ID NO: 1 (5'-cacttgtatggtcctgt-3') or SEQ ID NO: 2 (5'-gagtcgctagatgaggacctggata-3'). In this regard, in some embodiments, the siRNA is capable of binding a portion of a messenger RNA (mRNA) product (transcript) of a PFKFB4 gene or fragments thereof that comprises a nucleic acid sequence of SEQ ID NO: 1 or SEQ ID NO: 2.

In some embodiments, the siRNA comprises a nucleic acid sequence selected from the group consisting of SEQ ID NO: 6 (GGA GAG CGA CCA UCU UUA A), SEQ ID NO: 8 (CAC UUG UAU GGU CCU GUA A), SEQ ID NO: 10 (AUU AUC CUG AAU UUC CUC GUA GGU C), SEQ ID NO: 12 (UAU CCA GGU CCU CAU CUA GCG ACU C), and SEQ ID NO: 14 (UCU CGU UGA GGA CCU UCC ACU GUU C). In certain embodiments, the nucleic acid sequences are modified at the 5' end to comprise one or more dT residues, to enhance stability. In specific embodiments, SEQ ID NOS: 6 and 8 further comprise two dT residues at the 5' terminus. In some embodiments, the siRNA molecule can further comprise a second nucleic acid sequence that is complementary to the nucleic acid sequence selected from the group consisting of SEQ ID NO: 6, SEQ ID NO: 8, SEQ ID NO: 10, SEQ ID NO: 12, and SEQ ID NO: 14.

In some embodiments, the siRNA comprises a nucleic acid sequence selected from the group consisting of SEQ ID NO: 7 (UUA AAG AUG GUC GCU CUC C), SEQ ID NO: 9 (UUA CAG GAC CAU ACA AGU G), SEQ ID NO: 11 (GAC CUA CGA GGA AAU UCA GGA UAA U), SEQ ID NO: 13 (GAG UCG CUA GAU GAG GAC CUG GAU A), and SEQ ID NO: (GAA CAG UGG AAG GUC CUC AAC GAG A). In certain embodiments, the nucleic acid sequences are modified at the 5' end to comprise one or more dT residues, to enhance stability. In specific embodiments, SEQ ID NOS: 7 and 9 further comprise two dT residues at the 5' terminus. In some embodiments, the siRNA further comprises a second nucleic acid sequence that is complementary to the nucleic acid sequence selected from the group consisting of SEQ ID NO: 7, SEQ ID NO: 9, SEQ ID NO: 11, SEQ ID NO: 13, and SEQ ID NO: 15.

In some embodiments of the presently-disclosed methods, the PFKFB4 inhibitor is a short hairpin RNA (shRNA). In some embodiments, the shRNA comprises a nucleic acid sequence selected from the group consisting of SEQ ID NO: 4 (5'-GATCCG CACTTGTATGGTCCTGTAA TTCAAGAGA TTACAGGACCATACAAGTG TTTTTTGGAAA-3') and SEQ ID NO: 5 (5'-AGCTTTTCCAAAAAA CACTTGTATGGTCCTGTAA TCTCTTGAA TTACAGGACCATACAAGTG CG-3'). In some embodiments, an shRNA is provided that is designed against a PFKFB4 gene or fragments thereof. For example, in some embodiments, the shRNA is designed against a nucleic acid sequence comprising SEQ ID NO: 3 (5'-cacttgtatggtcctgt-3'). In this regard, in some embodiments, the shRNA is capable of binding a portion of a messenger RNA (mRNA) product (transcript) of a PFKFB4 gene or fragments thereof that comprises a nucleic acid sequence of SEQ ID NO: 3.

Further provided in some embodiments of the presently-disclosed subject matter are methods for treating a cancer in a cell. As used herein, the terms "treatment" or "treating" relate to any treatment of a cancer in a cell, including but not limited to prophylactic treatment and therapeutic treatment. As such, in some embodiments of the presently-disclosed methods of treating a cancer in a cell, the treating comprises reducing a proliferative activity of the cell, such as reducing the amount of, incidence of, or ability to sustain anchorage independent growth of a cell; decreasing production of fructose-2,6-bisphosphate (F2,6BP) in a cell; and/or reducing glycolytic flux in a cell.

In some embodiments, a method of treating a cancer in a cell is provided that comprises contacting the cell with an effective amount of a PFKFB4 inhibitor. In some embodiments, the cell is located within a subject. In some embodiments, the cancer is selected from the group consisting of lung cancer, colon cancer, breast cancer, and ovarian cancer.

In some embodiments of the presently-disclosed subject matter, a method of treating a cancer in a cell is provided, comprising contacting the cell with an effective amount of a PFKFB4 inhibitor, wherein the PFKFB4 inhibitor is an siRNA. In some embodiments, the siRNA is double-stranded. In some embodiments, the siRNA is designed against a PFKFB4 gene or fragments thereof. For example, in some embodiment, the siRNA is designed against a nucleic acid sequence comprising SEQ ID NO: 1 (5'-cacttgtatggtcctgt-3') or SEQ ID NO: 2 (5'-gagtcgctagatgaggacctggata-3'). In this regard, in some embodiments, the siRNA is capable of binding a portion of a messenger RNA (mRNA) product (transcript) of a PFKFB4 gene or fragments thereof that comprises a nucleic acid sequence of SEQ ID NO: 1 or SEQ ID NO: 2.

In some embodiments, the siRNA comprises a nucleic acid sequence selected from the group consisting of SEQ ID NO: 6 (GGA GAG CGA CCA UCU UUA A), SEQ ID NO: 8 (CAC UUG UAU GGU CCU GUA A), SEQ ID NO: 10 (AUU AUC CUG AAU UUC CUC GUA GGU C), SEQ ID NO: 12 (UAU CCA GGU CCU CAU CUA GCG ACU C), and SEQ ID NO: 14 (UCU CGU UGA GGA CCU UCC ACU GUU C). In certain embodiments, the nucleic acid sequences are modified at the 5' end to comprise one or more dT residues, to enhance stability. In specific embodiments, SEQ ID NOS: 6 and 8 further comprise two dT residues at the 5' terminus. In some embodiments, the siRNA molecule can further comprise a second nucleic acid sequence that is complementary to the nucleic acid sequence selected from the group consisting of SEQ ID NO: 6, SEQ ID NO: 8, SEQ ID NO: 10, SEQ ID NO: 12, and SEQ ID NO: 14.

In some embodiments, the siRNA comprises a nucleic acid sequence selected from the group consisting of SEQ ID NO: 7 (UUA AAG AUG GUC GCU CUC C), SEQ ID NO: 9 (UUA CAG GAC CAU ACA AGU G), SEQ ID NO: 11 (GAC CUA CGA GGA AAU UCA GGA UAA U), SEQ ID NO: 13 (GAG UCG CUA GAU GAG GAC CUG GAU A), and SEQ ID NO: (GAA CAG UGG AAG GUC CUC AAC GAG A). In certain embodiments, the nucleic acid sequences are modified at the 5' end to comprise one or more dT residues, to enhance stability. In specific embodiments, SEQ ID NOS: 7 and 9 further comprise two dT residues at the 5' terminus. In some embodiments, the siRNA further comprises a second nucleic acid sequence that is complementary to the nucleic acid sequence selected from the group consisting of SEQ ID NO: 7, SEQ ID NO: 9, SEQ ID NO: 11, SEQ ID NO: 13, and SEQ ID NO: 15.

In some embodiments of the presently-disclosed subject matter, a method of treating a cancer in a cell is provided, comprising contacting the cell with an effective amount of a PFKFB4 inhibitor, wherein the PFKFB4 inhibitor is a short hairpin RNA (shRNA). In some embodiments, the shRNA comprises a nucleic acid sequence selected from the group consisting of SEQ ID NO: 4 (5'-GATCCG CACTTGTATG-GTCCTGTAA TTCAAGAGA TTACAGGACCATA-CAAGTG TTTTTTGGAAA-3') and SEQ ID NO: 5 (5'-AGCTTTTCCAAAAAA CACTTGTATGGTCCTGTAA TCTCTTGAA TTACAGGACCATACAAGTG CG-3'). In some embodiments, an shRNA is provided that is designed against a PFKFB4 gene or fragments thereof. For example, in some embodiments, the shRNA is designed against a nucleic acid sequence comprising SEQ ID NO: 3 (5'-cacttgtatggtc-ctgt-3'). In this regard, in some embodiments, the shRNA is capable of binding a portion of a messenger RNA (mRNA) product (transcript) of a PFK.FB4 gene or fragments thereof that comprises a nucleic acid sequence of SEQ ID NO: 3.

Still further provided in some embodiments of the presently-disclosed subject matter are isolated nucleic acids. In some embodiments, an isolated nucleic acid is provided that comprises a sequence selected from the group consisting of SEQ ID NO: 4 and SEQ ID NO: 5. In some embodiments, an isolated nucleic acid is provided that comprises a sequence selected from the group consisting of SEQ ID NO: 6 and SEQ ID NO: 8. In other embodiments, an isolated nucleic acid is provided that comprises a sequence selected from the group consisting of SEQ ID NO: 7 and SEQ ID NO: 9.

EXAMPLES

The following examples are given by way of illustration and are in no way intended to limit the scope of the present invention.

Example 1

Cell Lines and Cell Culture

A549 lung adenocarcinoma cells, Colo-320 colon adenocarcinoma cells, MCF-7 breast adenocarcinoma cells and PC3 prostate adenocarcinoma cells were obtained from ATCC (Manassas, Va.). All cell lines were grown in DMEM containing 10% fetal calf serum (FCS) at 37° C. in 5% $CO_2$. PFKFB4 and scrambled shRNA stable clones were grown in DMEM containing FCS 10% and G418 (Mediatech, Herndon, Va.).

Example 2 siRNA and Transfection

The siRNA1 species was designed against the PFKFB4 gene (target sequence 5'-cacttgtatggtcctgt-3') using the Dharmacon siDesign tool and BLAST searched to confirm the target sequence was unique to the PFKFB4 gene. siRNA2 was obtained from Invitrogen (targeted against 5'-gagtcgcta-gatgaggacctggata-3'). Lamin A/C siRNA species (target sequence 5'-ctggacttccagaagaacatc-3') was obtained from Dharmacon (Lafayette, Colo.). Cells were transiently transfected with 10 nM siRNA using Lipofectamine RNAiMax (Invitrogen, Carlsbad, Calif.), following manufacturer's instructions, and harvested at 72 hours after transfection.

Example 3 shRNA and Transfection

Sense and antisense DNA oligonucleotides for PFKFB4 were designed with a hairpin against target sequence 5'-cact-tgtatggtcctgt-3' and obtained from IDT (Coralville, Iowa). The oligonucleotides were annealed and ligated into pSUPER vector (OligoEngine, Seattle, Wash.) following manufacturer's instructions. A549 lung adenocarcinoma cells were transfected with a short hairpin RNA (shRNA) expressing plasmid targeted against PFKFB4 (PFKFB4 shRNA) or a nonsense shRNA (control shRNA) by electroporation with the A549 Cell Line Nucleofector kit (Amaxa, Gaithersburg, Md.). The cells were transferred to tissue culture plates containing DMEM with 10% FCS and clones selected with G418 (500 μg/ml).

Example 4

Coexpression of the PFKFB Isozymes in Normal Human Tissue

Multiplex mRNA primers were custom synthesized (IDT) against human PFKFB 1-4 as described previously (Telang, S. et al., Ras transformation requires metabolic control by 6-phosphofructo-2-kinase, *Oncogene* 25:7225-34 (2006)). The multiplex potential of these primers was confirmed using cDNA species isolated from liver (PFKFB1), heart (PFKFB2), brain (PFKFB3) and testes (PFKFB4). Normal human tissues and matched tumor and adjacent normal tissues were analyzed using these primers as previously described and standard PCR conditions.

16 normal human organs and tissues were examined by RT-PCR using multiplex PCR primers specific for human PFKFB 1-4 (FIG. 1A). All the tissues were found to co-express mRNA species from 2 or more PFKFB isoforms. Results confirm PFKFB1 expression is increased in the liver and skeletal muscle, PFKFB2 expression is increased in the heart and PFKFB4 expression is increased in the testes.

Example 5

Overexpression of PFKFB4 in Multiple Tumor Tissues 20 tumors were examined and normal tissue specimens matched from the lung, colon, breast and ovary for expression of the four PFKFB mRNA species using multiplex RT-PCR. Results indicate that mRNA species from all four PFKFB isoforms were simultaneously expressed in all the tissues examined. Unexpectedly, results indicated a marked increase in PFKFB4 mRNA levels (and not PFKFB3 mRNA) in 17 of 20 (85%) tumors in comparison to adjacent matched normal tissues (FIG. 1B). Although the PFKFB3 isoform has been believed the dominant source of F2,6BP in multiple tumor types, the data support the conclusion that the PFKFB4 isoform performs a function in neoplastic tissues.

Example 6 siRNA Knockdown of PFKFB4 Decreases F2,6BP Production and Glycolytic Flux to Lactate by A549 Lung Adenocarcinoma Cells A549 cells were selected for in vitro studies. A549 cells express multiple PFKFB isoforms (PFKFB 2-4) at the mRNA and protein levels, have the capacity for anchorage independent growth in vitro and in vivo and, additionally, demonstrate a ras mutation at codon 12 (K-ras$^{G12S}$).

Intracellular F2,6BP levels between primary bronchial epithelial cells (NHBE, Lonza) and A549 lung adenocarcinoma cells were examined. Results indicated that A549 cells have ~2-fold higher steady-state concentration of F2,6BP than primary cells (F2,6BP: A549 cells 6.9±3 vs. NHBE cells 3.8±0.6 pmol/mg protein).

Figure 2:
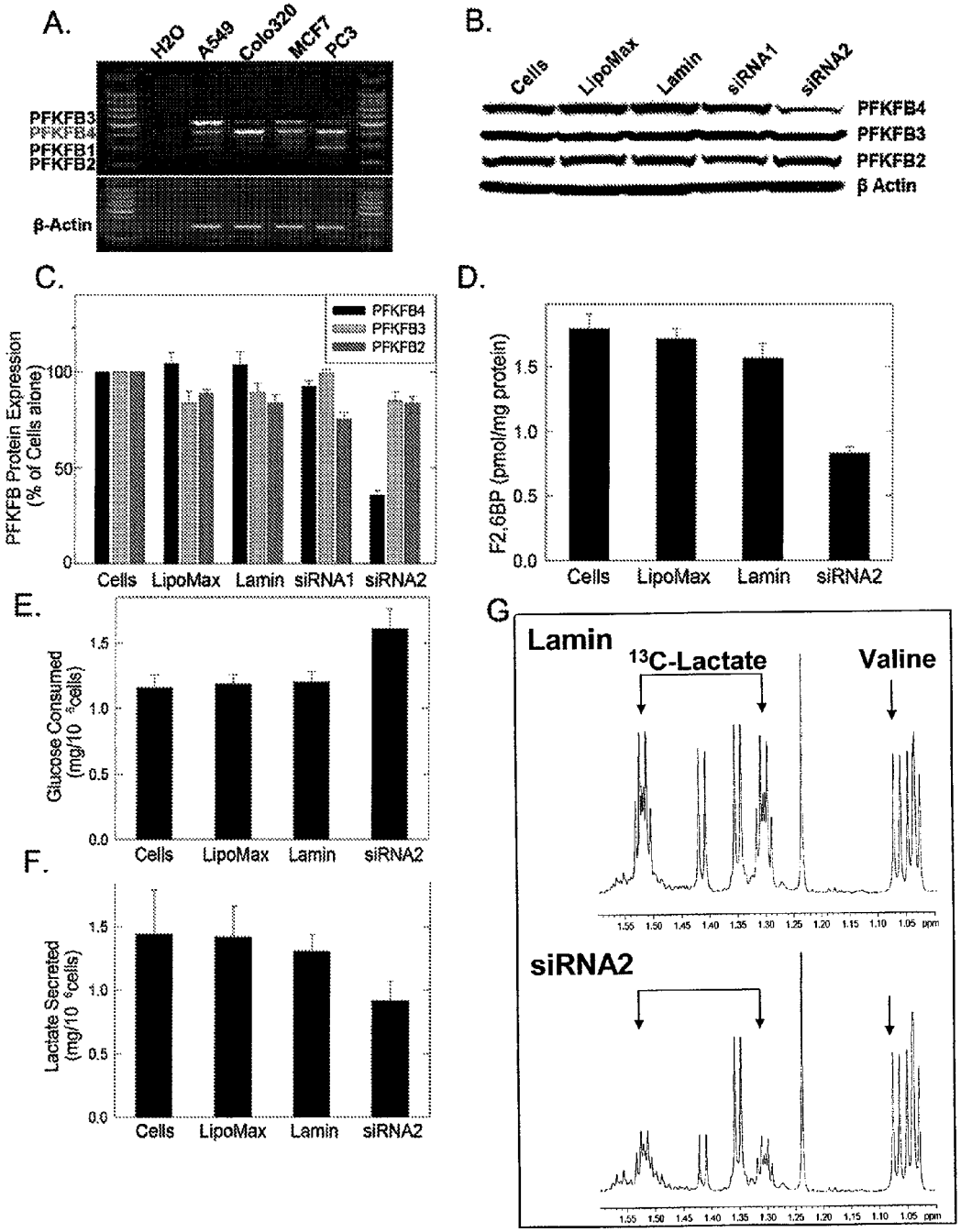
FIG. 2. siRNA mediated silencing of PFKFB4 reduces protein expression, F2,6BP production and glycolytic flux to lactate in A549 lung adenocarcinoma cells. (a) A549 alveolar adenocarcinoma cells, Colo320 colon adenocarcinoma cells, MCF7 breast adenocarcinoma cells and PC3 prostate adenocarcinoma cells were examined by multiplex RT-PCR analysis for PFKFB1-4 mRNA expression. (b) A549 cells were transfected with 10 nM siRNA against PFKFB4 (siRNA1, siRNA2) for 72 hrs. Protein extracted from the cells was resolved on a 12.5% gel, transferred to a PVDF membrane and expression of PFKFB4, PFKFB3, PFKFB2 and (3-Actin was examined by Western blot analysis. Lamin A/C was used as control. (c) Protein expression by Western blot was quantified by densitometric analyses, normalized to β-actin and expressed as percentage of control (cells alone). (d) $1\times10^6$ A549 cells transfected with 10 nM siRNA targeted against PFKFB4 (siRNA1 and siRNA2) for 72 hours were disrupted in 0.8 ml of 50 mM NaOH. Intracellular F2,6BP levels were measured by determining the allosteric activity of NaOH extracts on the activity of PFK-1. (e) Unconsumed glucose remaining in the media was measured 72 hrs after transfection with siRNA, expressed in mg/$10^6$ cells. (f) Lactate secreted into the media by the cells was measured 72 hrs after transfection with siRNA, expressed in mg/$10^6$ cells. (g) A549 cells pulsed with $^{13}C$-glucose were transfected with Lipofectamine RNAiMax alone, Lamin siRNA (control) or siRNA against the PFKFB4 ORF (siRNA2) for 72 h. Media was extracted with 10% TCA and analyzed by 1D NMR. Representative spectra from Lamin and siRNA2 are shown. Valine was used as an internal control. Data are expressed as the mean±SD of four experiments (b, c) and five experiments (e, f).

In order to examine the relationship between increased F2,6BP production and PFKFBP4 protein expression, A549 cells were transfected with 2 siRNA constructs (siRNA1 and siRNA2 targeted against the PFKFB4 3' UTR and open reading frame respectively) using an siRNA targeted against Lamin A/C as a control. After 72 hours of exposure, results indicated a significant decrease in PFKFB4 protein expression after treatment with siRNA2 by Western blot which was confirmed by densitometry (siRNA2: 39±2.8% of Lamin, p value <0.001) (FIGS. 2B and C).

Cells were treated with 0.25% trypsin-EDTA, washed in PBS, and lysed in 2×RIPA buffer. Protein samples were resolved on a 12.5% SDS-PAGE gel and transferred to a PVDF membrane. Membranes were blocked in TBS-Tween 20 (1%) containing 5% milk. Rabbit anti-PFKFB4 C-terminus polyclonal antibody, rabbit anti-PFKFB3 C-terminus polyclonal antibody, rabbit anti-PFKFB2 C-terminus polyclonal antibody (all 1:250, Abgent, San Diego, Calif.) or mouse anti-β-actin (1:5000, Sigma, St. Louis, Mo.) were re-suspended in 10 ml of TBS-Tween 20, (3% milk) and incubated with the membrane overnight (PFKFB2-4) or for 1 hour (β-actin). Secondary antibodies used were HRP conjugated goat anti-rabbit or anti-mouse (1:8000, Pierce Biotechnology).

Importantly, no decrease in expression of either PFKFB2 or PFKFB3 proteins (both of which are co-expressed in A549 cells) was found by either siRNA species targeted against PFKFB4. The siRNA2 construct was selected for further experimentation.

Example 7

Effect of siRNA Mediated Silencing of PFKFB4 on Intracellular F2,6BP Levels

An equal number of cells were trypsinized, washed twice with PBS, and collected to measure total intracellular F2,6BP as previously described (Van Schaftingen, et al., A kinetic study of pyrophosphateL fructose-6-phosphate phophotranserase from potato tuber: Application to a microassay of fructose 2,6-bisphosphate, *Eur. J. Biochem.* 129:191-95 (1982)). The F2,6BP concentration was normalized to total cellular protein as measured by the bicinchoninic acid (BCA) assay (Pierce Biotechnology, Rockford, Ill.).

Results show that treatment with PFKFB4 siRNA caused a ~50% decrease in F2,6BP production compared with Lamin siRNA (F2,6BP: siRNA2 0.83±0.05 vs. Lamin 1.57±0.11 pmol/mg protein, p value <0.05) (FIG. 2D). These data indicate that PFKFB4 is required for the production of F2,6BP. As an indicator of glycolytic flux, lactic acid secretion into the culture media by A549 cells was measured following PFKFB4 siRNA treatment for 72 hours using a lactate oxidase assay.

Lactate concentrations in the media were measured using a lactate oxidase-based assay read at 540 nm (Trinity, Wicklow, Ireland). Glucose concentrations were measured using a hexokinase-glucose-6-phosphate dehydrogenase enzymatic assay read at 340 nm (Sigma, St. Louis, Mo.). All lactate and glucose data were normalized to cell number.

Results show that treatment with PFKFB4 siRNA caused a ~30% decrease in lactic acid secretion (lactate secreted in mg/10$^6$ cells: siRNA2 0.91±0.15 vs. Lamin 1.31±0.2, p value <0.05) (FIG. 2F) accompanied by decreased glucose consumption (FIG. 2E). To confirm results, the channeling of fully labeled $^{13}$C-glucose to lactate by A549 cells treated with PFKFB4 siRNA for 72 hours was examined using one-dimensional nuclear magnetic resonance spectroscopy. Results indicate that PFKFB4 siRNA treated cells converted significantly less glucose to lactate than cells treated with Lamin siRNA or treated with the transfection reagent alone (representative 1D spectra from Lamin and siRNA2 treatment shown, FIG. 2G). These results confirm that suppression of PFKFB4-catalyzed F2,6BP production is causing a decrease in the metabolic flux to lactate.

Example 8 siRNA Silencing of the PFKFB4 Isozyme Decreases Cell Proliferation and the Capacity for Anchorage Independent Growth In Vitro Neoplastic cells depend on glycolysis for the production of critical biosynthetic intermediates for cellular proliferation. It was therefore predicted that the decrease in glycolytic flux caused by silencing PFKFB4 would lead to decreased cellular proliferation.

In order to examine the effect of silencing PFKFB4, a feeder layer of 0.6% agarose (Agar Noble, Becton Dickinson, Sparks, Md.) in DMEM was plated in 6 cm plates. $2.5 \times 10^4$ cells were re-suspended in 0.3% agarose in DMEM and placed on top of the feeder layer. Cells were allowed to grow at 37° C. in 5% $CO_2$ and media replenished once a week until colonies became visible. Colonies were stained with MTT [3-(4,5-dimethylthiazol-2-yl)-2,5-diphenyl tetrazolium bromide] and counted in three random 1 $cm^2$ areas per plate under 40× magnification.

Figure 4:
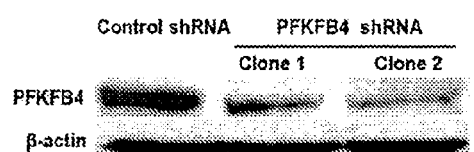
FIG. 4. Short hairpin RNA (shRNA) mediated silencing of PFKFB4 decreases F2,6BP concentration and limits capacity for anchorage-independent growth. A549 lung adenocarcinoma cells were transfected with a short hairpin RNA (shRNA) expressing plasmid targeted against PFKFB4 3'UTR (pSuper/PFKFB4) by electroporation and clones were selected using G418. A nonsense shRNA was used as a control. (a) After selection, protein was extracted from cells expressing the control shRNA or PFKFB4 shRNA (Clone 1 and 2) and PFKFB4 protein expression was examined by Western blot. (b) $10^6$ A549 cells expressing the control shRNA or PFKFB4 shRNA (Clone2) and intracellular F2,6BP levels were measured. (c) $2\times10^4$ cells were plated on 6 cm dishes (n=3) and colonies formed in soft agar were photographed and (d) enumerated at 15 days (data as mean±SD of four experiments) (b and d).
Figure 4:
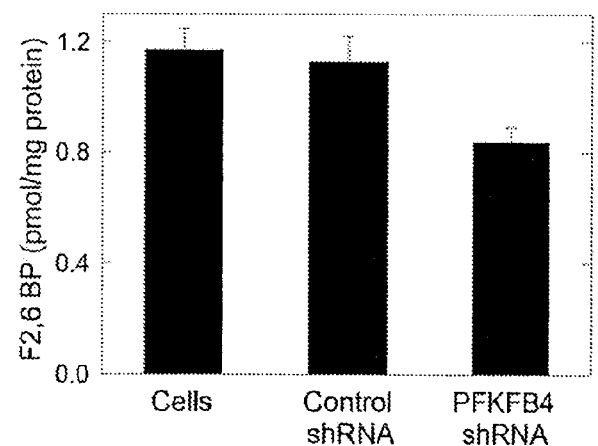
Figure 4:
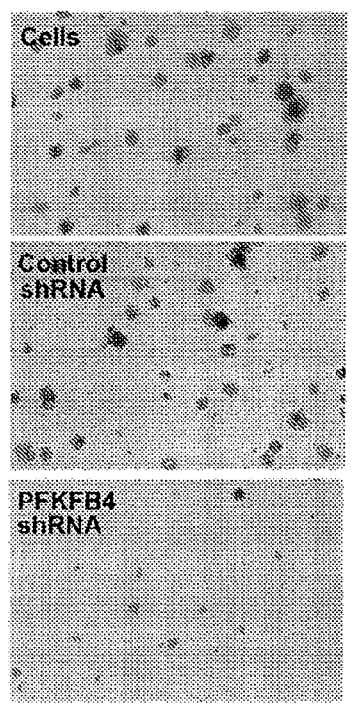
Figure 4:
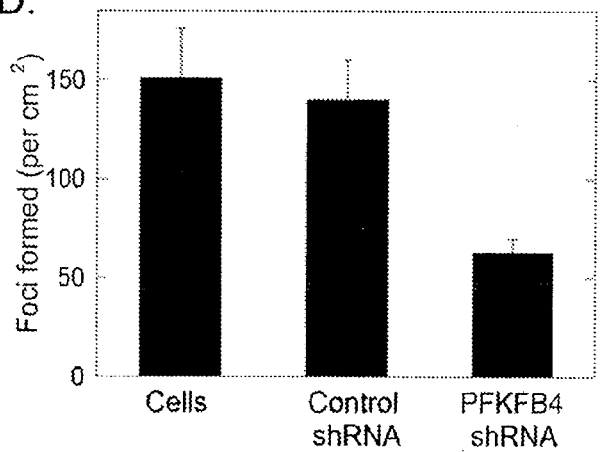

Cells were counted 72 hours after transfection with siRNA and results showed an approximately 30% decrease in the number of PFKFB4 siRNA treated cells in comparison with Lamin siRNA treatment (cell counts, $\times 10^4$/ml: siRNA2 65.8±4.1 vs. Lamin 95.9±2.9, p value <0.05) (FIG. 4A).

Growth in soft agar requires anchorage independence and the ability to survive growth as a mass similar to a tumor in vivo. A549 cells were treated with siRNA for 72 hours, equal numbers of treated cells were plated in soft agar and their growth followed for 21 days. Results indicated that PFKFB4 siRNA treated cells produced markedly decreased numbers of colonies in soft agar. In addition, the colonies that did form were smaller than those formed by either cells treated with a siRNA targeted against Lamin or transfection reagent alone (colonies formed at 21 days, per $cm^2$: siRNA2 6±2 vs. Lamin 73.6±6, p value <0.05).

Example 9 siRNA Knockdown of PFKFB4 Attenuates Growth of Tumors in Athymic Mice

Anchorage independent growth in soft agar often predicts growth of tumors in vivo. In order to investigate the ability of siRNA-induced silencing of PFKFB4 to inhibit tumor growth in vivo, A549 cells were treated with siRNA against PFKFB4 or Lamin for 72 hours. Cells were collected from exponential growth phase culture in DMEM supplemented with 10% fetal calf serum. Cells were washed twice and re-suspended in PBS ($5 \times 10^7$ cells/ml). Groups of CD1 nude female mice (20 gm) were injected subcutaneously into the flanks with 0.10 ml of the cell suspension ($5 \times 10^6$ cells). The tumors were followed from the time of appearance until 40 days. Tumor masses were determined in a blinded fashion with Vernier calipers according to the following formula: weight (mg)=(width, m)$^2$×(length, m)/2.

Figure 3:
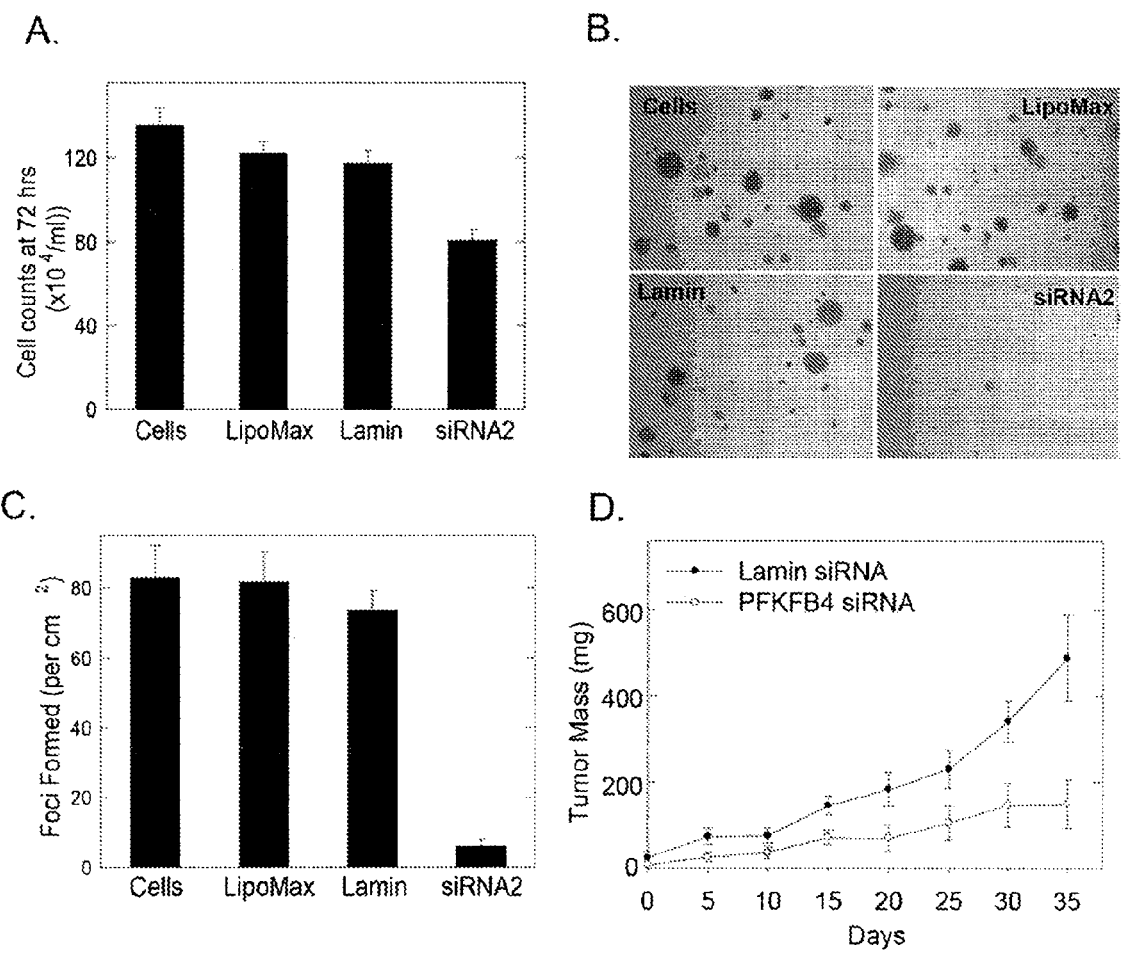
FIG. 3. Transient siRNA mediated knockdown of PFKFB4 significantly decreases anchorage-independent growth in vitro and in vivo. A549 lung adenocarcinoma cells were transfected with 10 nM siRNA targeted against PFKFB4 (siRNA2). Lamin A/C siRNA used as a control. (a) Viable and non-viable cells were enumerated at 72 hours by Trypan blue exclusion using a hemacytometer. (b) After 72 hours of siRNA exposure, $2\times10^4$ cells were plated on 6 cm dishes (n=3) and colonies formed in soft agar were photographed and (c) were counted at 15 days (data as mean±SD, n=3). (d) A549 lung adenocarcinoma cells were transfected with 10 nM siRNA targeted against PFKFB4 (siRNA2) and $6\times10^6$ cells (in 100 µl) were implanted subcutaneously into female CD1 (nu/nu) athymic mice. A549 cells transfected with 10 nM Lamin A/C siRNA were used as a control. Tumor growth was monitored with microcalipers for 35 days and volumes calculated according to the formula [tumor volume=length× (width)2/2]. (n=8, data as mean of 2 experiments±SD).

Results indicated that the tumors formed by PFKFB4 siRNA treated cells were significantly smaller than those formed by A549 cells treated with Lamin siRNA (tumor volumes at 35 days: PFKFB4 siRNA 148.6±55.7 $mm^3$ vs. Lamin siRNA 488.66±100.8 $mm^3$, p value <0.05) (FIG. 3D).

Example 10 shRNA Mediated Silencing of PFKFB4 Decreases F2,6BP Concentration and Limits the Capacity for Anchorage Independence In order to evaluate the effects of a more prolonged knockdown of PFKFB4, A549 cells were transfected with a short hairpin RNA (shRNA) expressing plasmid targeted against PFKFB4 (pSuper/PFKFB4) by electroporation. Cells transfected with a plasmid expressing a scrambled sequence and untransfected A549 cells were used as controls. Following antibiotic selection in G418, PFKFB4 protein expression was examined in cells stably transfected with the scrambled siRNA and cells transfected with PFKFB4 shRNA and knockdown of the PFKFB4 protein was confirmed (FIG. 4A). Clone 2, which demonstrated greater knockdown of the PFKFB4 protein, was selected for further experimentation. F2,6BP concentration was measured in the cells and found that shRNA mediated silencing of PFKFB4 decreased the production of F2,6BP by ~30% compared with the scrambled shRNA (F2,6BP: PFKFB4 shRNA 0.8366±0.56 vs. scrambled shRNA 1.126±0.09, pmol/mg protein, p value <0.05). Similar to the siRNA treated A549 cells, this decrease in F2,6BP production was accompanied by a significant decrease in the both the number and the diameter of colonies formed in soft agar at 21 days (colonies formed per $cm^2$: PFKFB4 shRNA 63±7 vs. control shRNA 143±20, p value <0.05).

Example 11 shRNA Mediated Silencing of PFKFB4 Limits Tumor Formation In Vivo

Figure 5:
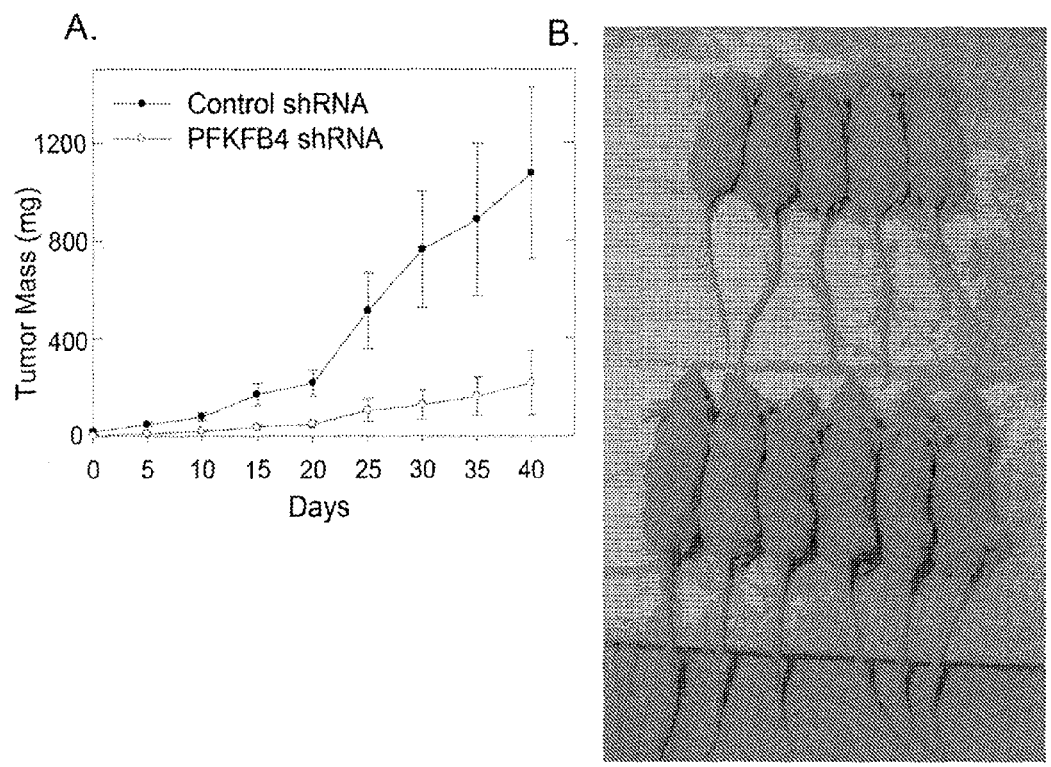
FIG. 5. PFKFB4 shRNA transfected A549 cells exhibit decreased tumorigenesis in athymic mice. (a) PFKFB4 shRNA (clone 2) transfected cells ($5\times10^6$ cells in 100 µl) were implanted subcutaneously into female CD1 (nu/nu) athymic mice. Tumor growth was monitored with microcalipers for 40 days and volumes calculated according to the formula [tumor volume=length×(width2/2)]. Nonsense shRNA transfected cells were used as a control (n=8, data as mean of 2 experiments±SD). (b) Representative photograph of tumor bearing mice. PFKFB4 shRNA implanted mice above and control shRNA treated mice below.

In order to further confirm the capacity of the PFKFB4 shRNA to inhibit anchorage independent growth, $5 \times 10^6$ A549 cells transfected with either a control (scrambled) shRNA or PFKFB4 shRNA were subcutaneously injected into the flanks of athymic mice and the development of tumors was followed for 40 days. Results show that the tumors formed by PFKFB4 shRNA expressing cells were significantly smaller than those formed by cells expressing the control shRNA (tumor volumes 40 days after implantation: PFKFB4 shRNA 217.9±130.9 $mm^3$ vs. control shRNA 1076.8±351 $mm^3$, p value <0.05) (FIG. 5A).

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. A method of reducing expression of 6-phosphofructo-2-kinase/fructose-2,6-bisphosphatase 4 (PFKFB4), comprising contacting a cell with an effective amount of a PFKFB4 inhibitor, wherein the PFKFB4 inhibitor is a small interfering RNA (siRNA) having a first nucleic acid sequence and a second nucleic acid sequence, wherein said first nucleic acid sequence consists of a nucleic acid sequence selected from the group consisting of SEQ ID NO: 8 and SEQ ID NO: 9.

2. The method of claim 1, wherein said second nucleic acid sequence is complementary to the first nucleic acid sequence, and wherein the second nucleic acid sequence consists of SEQ ID NO: 9 when the first nucleic acid consists of SEQ ID NO: 8, and wherein the second nucleic acid sequence consists of SEQ ID NO: 8 when the first nucleic acid sequence consists of SEQ ID NO: 9, and wherein the siRNA is double-stranded.

3. The method of claim 1, wherein the siRNA is designed against a nucleic acid sequence comprising SEQ ID NO: 1.

4. A method of treating a cancer cell, comprising contacting the cell with an effective amount of a PFKFB4 inhibitor, wherein the PFKFB4 inhibitor is a small interfering RNA (siRNA) having a first nucleic acid sequence and a second nucleic acid sequence, wherein said first nucleic acid sequence consists of a nucleic acid sequence selected from the group consisting of SEQ ID NO: 8 and SEQ ID NO: 9.

5. The method of claim 4, wherein the cell is located within a subject.

6. The method of claim 4, wherein the cancer is selected from the group consisting of lung cancer, colon cancer, breast cancer, and ovarian cancer.

7. The method of claim 4, wherein the treating comprises reducing a proliferative activity of the cell.

8. The method of claim 4, wherein the treating comprises decreasing production of fructose-2,6-bisphosphate (F2, 6BP).

9. The method of claim 4, wherein the treating comprises reducing glycolytic flux in the cell.

10. The method of claim 4, wherein said second nucleic acid sequence is complementary to the first nucleic acid sequence, and wherein the second nucleic acid sequence consists of SEQ ID NO: 9 when the first nucleic acid consists of SEQ ID NO: 8, and wherein the second nucleic acid sequence consists of SEQ ID NO: 8 when the first nucleic acid sequence consists of SEQ ID NO: 9, and wherein the siRNA is double-stranded.

11. The method of claim 4, wherein the siRNA is designed against a nucleic acid sequence comprising SEQ ID NO: 1.

12. A method of reducing expression of 6-phosphofructo-2-kinase/fructose-2,6-bisphosphatase 4 (PFKFB4), comprising contacting a cell with an effective amount of a PFKFB4 inhibitor, wherein the PFKFB4 inhibitor is a small hairpin RNA (shRNA) comprising a nucleic acid sequence that is SEQ ID NO: 4 or SEQ ID NO: 5.

13. A method of treating a cancer cell, comprising contacting the cell with an effective amount of a PFKFB4 inhibitor, wherein the PFKFB4 inhibitor is a small hairpin RNA (shRNA) comprising a nucleic acid sequence that is SEQ ID NO: 4 or SEQ ID NO: 5.

* * * * *

UNITED STATES PATENT AND TRADEMARK OFFICE
CERTIFICATE OF CORRECTION

PATENT NO.       : 8,283,332 B2
APPLICATION NO.  : 12/761773
DATED            : October 9, 2012
INVENTOR(S)      : Sucheta Telang et al.

Page 1 of 1

It is certified that error appears in the above-identified patent and that said Letters Patent is hereby corrected as shown below:

Claim 10, column 18, line 59, change "nucleic acid consists of" to --nucleic acid sequence consists of--.

Signed and Sealed this
Fourth Day of December, 2012

David J. Kappos
*Director of the United States Patent and Trademark Office*